United States Patent
Li et al.

(10) Patent No.: US 7,284,453 B2
(45) Date of Patent: Oct. 23, 2007

(54) METHOD AND APPARATUS FOR MAXIMIZING LIQUID ASPIRATION FROM SMALL VESSELS

(75) Inventors: William Weigong Li, Miami, FL (US); Marco Zuleta, Miami, FL (US); Pablo Larrea, Miami Beach, FL (US); Santiago Galvez, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 49 days.

(21) Appl. No.: 11/183,145

(22) Filed: Jul. 15, 2005

(65) Prior Publication Data

US 2007/0012123 A1     Jan. 18, 2007

(51) Int. Cl.
*G01N 1/14* (2006.01)
*F04B 49/02* (2006.01)
*F04B 49/06* (2006.01)
*B01L 3/02* (2006.01)

(52) U.S. Cl. ............... 73/863.01; 73/864.11; 73/864.24; 436/180; 417/279

(58) Field of Classification Search ............ 73/863.01, 73/864.11, 864.24; 436/180; 422/926; 417/279, 282
See application file for complete search history.

(56) References Cited

U.S. PATENT DOCUMENTS

| | | | |
|---|---|---|---|
| 3,473,380 A * | 10/1969 | Young et al. .............. 73/304 C |
| 4,003,260 A * | 1/1977 | Catoul ...................... 73/863.01 |
| 4,679,326 A * | 7/1987 | Takizawa et al. ............. 33/832 |
| 5,102,623 A * | 4/1992 | Yamamoto et al. .. 73/864.24 X |
| 5,116,114 A * | 5/1992 | Nakamura et al. .......... 351/205 |
| 5,133,392 A | 7/1992 | Hamann et al. ................ 141/1 |
| 5,275,951 A * | 1/1994 | Chow et al. .................. 436/50 |
| 5,895,630 A * | 4/1999 | Skaborn et al. ...... 73/864.24 X |
| 6,234,033 B1 * | 5/2001 | Eipel ......................... 73/864.25 |
| 6,254,832 B1 * | 7/2001 | Rainin et al. ........... 436/180 X |
| 6,270,726 B1 | 8/2001 | Tyberg et al. ........... 436/180 X |
| 6,363,802 B1 | 4/2002 | Grippo et al. ........... 73/864.24 |
| 2001/0027269 A1 * | 10/2001 | Tanaka ........................ 600/368 |
| 2001/0047692 A1 * | 12/2001 | Lipscomb et al. ........ 73/864.25 |
| 2003/0194349 A1 | 10/2003 | Carey et al. |

(Continued)

FOREIGN PATENT DOCUMENTS

JP          1-97865 A          4/1989

*Primary Examiner*—Thomas P. Noland
(74) *Attorney, Agent, or Firm*—Warren W. Kurz; Mitchell E. Alter

(57) ABSTRACT

Apparatus and method for aspirating liquid from a container, e.g., a test tube or other vessel, includes apparatus for sensing that an aspiration probe tip is contacting the inside bottom wall of the container, whereby a maximum volume of liquid can be aspirated from the container. According to the invention, an encoder is mounted on the driven member of a motor (e.g., on a rotatably-driven drive shaft or a nut of a stepper or D.C. motor, or on a linearly-driven shaft of a linear actuator) used to rectilinearly advance the probe tip into the container. Such encoder produces a series of pulses indicating the speed and/or linear position of the probe tip. A motor controller responds to a predetermined change in pattern of pulses from the encoder indicating that movement of the probe tip has been resisted by the vessel bottom, whereby further movement of the driven member and of the probe connected thereto is arrested, and the probe tip remains in contact with the vessel bottom.

5 Claims, 2 Drawing Sheets

U.S. PATENT DOCUMENTS

2004/0096368 A1* 5/2004 Davis et al. ............... 422/104
2005/0013744 A1 1/2005 Nagai et al.
2006/0216208 A1* 9/2006 Li et al. .................... 422/100

* cited by examiner

METHOD AND APPARATUS FOR MAXIMIZING LIQUID ASPIRATION FROM SMALL VESSELS

BACKGROUND OF THE INVENTION

1. Field of the Invention

The present invention relates to improvements in apparatus for aspirating liquids, e.g. biological specimens, from small vessels, e.g. test tubes or vials, for processing. More specifically, this invention relates to improvements in apparatus for sensing contact between the tip of a liquid-aspiration probe and the bottom of a vessel from which liquid is to be aspirated. The invention is particularly useful in automated hematology instruments for extracting the last useful blood sample volume from test tubes and the like for analysis.

2. The Prior Art

In conducting tests on biological liquids, e.g., blood, it is common to employ automated instruments to extract liquid specimens from small vessels, such as test tubes and the like. Such instruments typically include a movably-mounted sample aspiration probe that is adapted to be driven downwardly into the interior of a vertically-oriented test tube to a position in which the aspiration tip is below the level of sample liquid in the tube. In cases where the liquid sample is relatively small, such as a blood sample drawn from an infant, it is often necessary to advance the probe tip into near or virtual contact with the tube bottom in order to aspirate a sufficient volume of sample for testing. Since sample tubes can vary significantly in size, it can be problematic to consistently achieve probe tip/tube bottom contact without risking breakage of the tube. This problem is exacerbated when the probe tip is sharpened to puncture a rubber seal atop the tube.

In the commonly assigned U.S. Pat. No. 6,363,802 to Grippo et al., different types of apparatus are disclosed for maintaining contact between an aspiration probe tip and a tube bottom during a liquid aspiration process. In one embodiment, the tube is supported on a horizontal platform that is vertically movable and spring-biased towards a nominal rest position. As the aspiration probe is driven downwardly by a stepper motor or the like, the eventual contact between the probe tip and the tube bottom exerts a downward force on the tube-supporting platform, such force acting to physically displace the platform from its rest position. This displacement of the platform is directly sensed by a photo-electric sensor or the like, and an output signal from the sensor serves, through suitable circuitry, to arrest further operation of the stepper motor and to maintain the probe tip in contact with the tube bottom throughout the liquid aspiration. In a second embodiment, rather than supporting the tube on a movable platform, the tube is positioned on a fixed platform, and the forcible interaction between the probe tip and tube bottom is indirectly sensed by monitoring the back-emf in a winding of a D.C. motor used to advance the aspiration probe into the tube. While both of these embodiments can readily accomplish their intended purpose of sensing contact between the probe tip and container bottom, each may be problematic from different standpoints. For example, the movable platform approach tends to be relatively complex from a mechanical standpoint, and while the back-emf-sensing approach is mechanically simple, it can be relatively imprecise and less reflective of the actual force being applied between the probe tip and the container bottom.

SUMMARY OF THE INVENTION

In view of the foregoing discussion, an object of this invention is to provide, in a liquid aspiration apparatus of the type described, an improved method and apparatus for detecting contact between the tip of an aspiration probe and the bottom of a liquid-containing vessel, such as a test tube or the like, whereby the maximum volume of liquid can be extracted from the vessel.

Compared to the prior art approaches to bottom-detection discussed above, the liquid aspirating apparatus of the invention is improved from the standpoint that it combines the direct-sensing advantage of the above-noted movable-platform approach with the simplicity of the afore-described back-emf-monitoring approach. Yet, it overcomes the noted disadvantages of each of these approaches.

In accordance with a preferred embodiment of the invention, apparatus for aspirating a volume of liquid from a liquid-containing vessel comprises; (a) a liquid-aspirating probe having a tip through which liquid in a vessel can be aspirated; (b) a motor comprising a movably-mounted driven member for advancing the probe tip into a vessel containing liquid to be aspirated as such driven member is driven by the motor in a first direction; (c) means operatively coupled to the driven member for producing a signal indicating the speed of movement and/or position of such driven member; and (d) a motor controller, responsive to such signal, for arresting further movement of the driven member in the event the signal indicates that an advancement of the probe tip has been resisted by contact with a wall of the vessel. Preferably the signaling means comprises an encoder that is operatively coupled to the driven member. The motor controller responds to a predetermined change in pattern of pulses from the encoder indicating that movement of the probe tip has been resisted by the vessel bottom, whereby further movement of the driven member and the probe connected thereto is arrested.

In accordance with another aspect of the invention, a method for aspirating a volume of liquid from a liquid-containing vessel comprises the steps of; (a) providing a liquid-aspirating probe having a tip through which liquid in a vessel can be aspirated; (b) selectively operating a motor to advance the probe tip into a vessel containing liquid to be aspirated, such motor having coupled thereto an encoder that provides a series of pulses indicating the speed of advance and/or position of the probe tip; and (c) arresting operation of the motor in response to an indication by the series of pulses produced by the encoder that movement of the probe tip has been resisted by contact with a wall of the vessel.

The invention and its advantages will be better understood from the ensuing detailed description of preferred embodiments, reference being made to the accompanying drawings wherein like reference characters denote like parts.

DETAILED DESCRIPTION OF PREFERRED EMBODIMENTS

Figure 1:
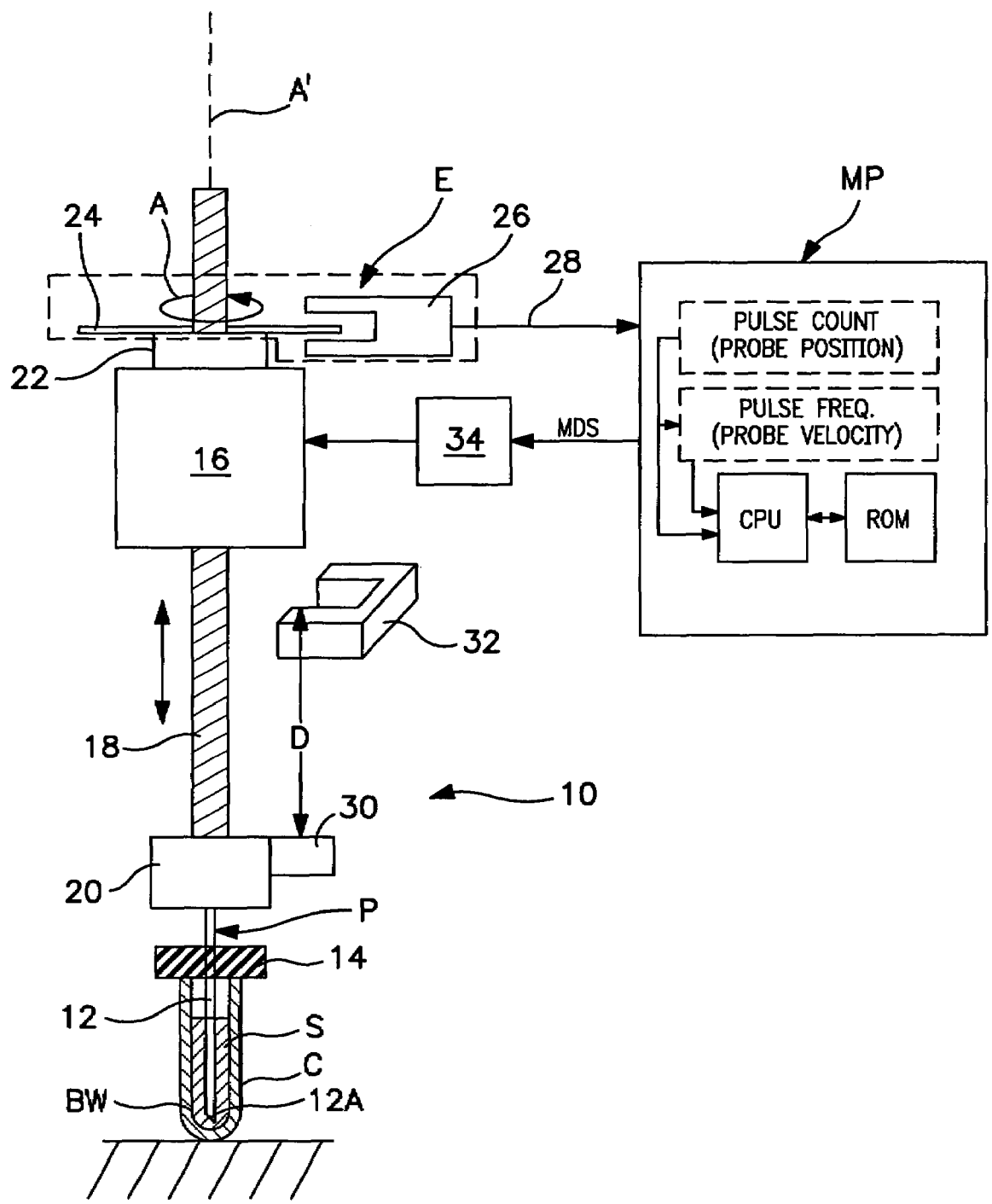
FIG. 1 is a schematic illustration of a preferred apparatus for sensing contact between the tip of an aspiration probe and the inside bottom of a liquid-containing vessel.

Referring now to the drawings, FIG. 1 schematically illustrates a liquid-aspiration apparatus 10 embodying a preferred form of the invention. Apparatus 10 generally comprises a vertically-movable aspiration probe P that is selectively operable to extract a predetermined volume of a liquid sample S contained by a test tube or other container C, and to convey such sample volume towards a utilization device (not shown), e.g., a blood analyzer. The aspiration probe typically comprises a hollow cannula 12 having a sharpened distal end 12A. In a well-known manner, the aspiration probe is operatively connected to the suction end of a vacuum pump (not shown) that serves to selectively create a negative pressure (vacuum) within the cannula in order to aspirate sample liquid into the cannula and into the liquid conduit(s) to which it is fluidly connected. The sharpened distal end of the probe is adapted to puncture a rubber seal 14 positioned atop the sample container and to enter the sample volume as the probe is moved vertically downward, as viewed in the drawing, towards the bottom wall BW of the container. Vertical movement of the aspiration probe is preferably controlled, in a known manner, by a stepper motor 16 that, in the embodiment illustrated, selectively operates to rectilinearly and incrementally advance a precision lead screw 18 to which the aspiration probe is operatively connected via a linkage 20. Rectilinear vertical movement of lead screw 18 is achieved via a rotatably-mounted nut 22 having an internal thread that drivingly-engages the external thread on the lead screw. Nut 22 is an integral part of the stepper motor, and it is rotatably driven by the stepper motor to achieve incremental rotation of the nut about the nut axis A which, in this case, is vertically oriented. Thus, as motor 16, which is normally fixed with respect to its supporting structure, is operated to rotate nut 22 in one direction or the other, lead screw 18 moves vertically, in one direction or the other, without itself rotating. Preferred apparatus for guiding such vertical movement of the aspiration probe is disclosed in the commonly assigned U.S. application Ser. No. 11/088,157 filed on Mar. 23, 2005, in the names of William Li et al. and entitled, "Apparatus for Aspirating Liquids from Sealed Containers, the subject matter of which is incorporated herein by reference.

In the above-noted patent application, it is noted that the stepper motor used to advance the aspiration probe may comprise an encoder that serves to precisely control the movement of the probe tip. As the above-noted nut of the stepper motor rotates under the direction of a suitably-programmed microprocessor, the encoder will monitor such movement and typically provide a train of pulses having a frequency reflecting the actual speed of motor (nut) rotation. The microprocessor can then process the encoder output to determine the actual linear acceleration and velocity of the probe, and this information can be compared with an intended "velocity profile" which is initially used to drive the stepper motor in such a manner as to theoretically achieve a desired movement of the probe for a given sample container size. If the actual velocity profile, as determined from the encoder output, agrees with the intended velocity profile, the motor system is known to be performing as intended. If the actual and intended velocity profiles are in disagreement, then an error signal can be generated to indicate a need to take corrective action.

In order to maximize the volume of liquid that can be aspirated from the sample container, it will be appreciated that it is essential to reliably position the distal end of the aspiration probe P adjacent the inside bottom wall BW of the sample container C. Otherwise, liquid below the tip of the aspiration probe will remain in the container after aspiration. As indicated above, prior art attempts to consistently achieve such probe tip/container bottom contact have required relatively complex moving mechanical mechanisms, or have used electrical schemes in which the probe tip/container bottom contact is only indirectly (and sometimes imprecisely) sensed.

Now, in accordance with the present invention, vertical movement of the aspiration probe to repeatedly and reliably locate the aspiration probe tip 12A adjacent the inside bottom wall BW of the sample container prior to sample aspiration is achieved by monitoring the output of an encoder E used to monitor the velocity profile of the motor's driven member (e.g., the rotatably driven nut 22 of motor 16) and, thus, the linear motion and/or position of the aspiration probe. As shown in the drawing, the encoder comprises an encoder wheel or disk 24 mounted for rotation (as indicated by the arrow A) with the rotatably-driven nut 22, and a photo-electric sensor component 26 positioned to sense indicia on the encoder disk as the disk rotates about the nut axis A'. The encoder disk is typically transparent to light, and the indicia thereon is commonly in the form of a plurality of equally-spaced and radially-extending light-blocking marks which serve to intensity-modulate a light beam (provided by the sensor component 26) that is projected through the disk. This light beam, as modulated in intensity by the indicia passing through it, is sensed by a light-sensitive array within the sensor component 26, and its output 28 is transmitted to a microprocessor MP. The encoder output 28 comprises a train of pulses or "ticks," each pulse representing a predetermined angular rotation of the disk (and nut 22), and, hence, a predetermined rectilinear movement of the lead screw 18, and of the aspiration probe connected thereto. By counting the encoder's output pulses, the central processing unit (CPU) of the microprocessor can compute the distance D the probe moves from its "home" position where a flag 30 carried by housing 20 is sensed by a photoelectric or magnetic sensor 32. In the home position, the probe tip is located above the container seal 20 to enable the container to be removed and replaced with another sample container. By continuously monitoring the encoder output for the production of pulses within a preset timing window, typically of the order of time required to produce two consecutive timing pulses, (e.g., about 5-10 milliseconds), the microprocessor can determine when the probe tip has contacted the container bottom. At this time, the container bottom will resist further downward movement of the probe tip, and no further pulses will be generated by the encoder. When the microprocessor does not receive an encoder pulse within the preset timing window, the microprocessor will immediately interrupt the motor drive signal MDS applied to the motor driver 34, and the motor 16 will be de-energized. At this time, the probe tip will remain in contact (or virtual contact) with the container bottom, and sample aspiration can commence.

Figure 2:
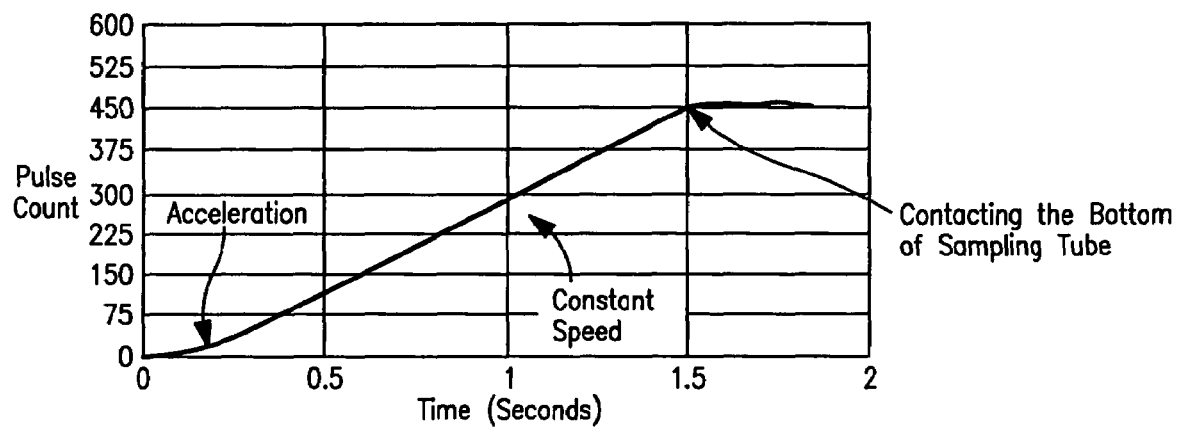
FIG. 2 is a waveform illustrating the accumulated output of an encoder used to monitor the motor armature position during movement of an aspiration probe into a liquid-containing vessel.

In the graph of FIG. 2, the number of pulses or "ticks" produced by the encoder 26 in the FIG. 1 apparatus is plotted as a function of time. As shown, the number of pulses accumulated gradually increases during an acceleration phase, after which the curve becomes substantially linear, indicating that the probe has attained a constant speed. As the probe moves at constant speed, the rotatably-driven nut 22 of motor 16 rotates at a substantially constant velocity, and the encoder pulses are received at a substantially constant rate until the probe tip encounters the container bottom. At this time, no further pulses are accumulated and, after a predetermined time interval, e.g., about 4-8 msec., the microprocessor determines that the probe tip is contacting the container bottom. The microprocessor then immediately de-energizes motor 16 and initiates sample aspiration.

Figure 3:
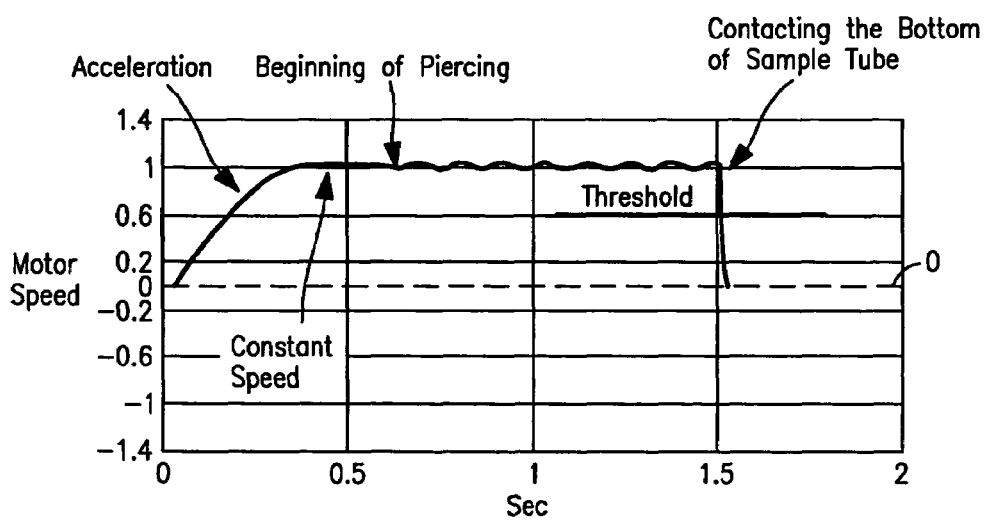
FIG. 3 is a waveform illustrating the angular velocity of a motor armature used to advance an aspiration probe into a sealed, liquid-containing vessel.

In the graph of FIG. 3, another scheme is shown for detecting probe tip/container bottom contact. Here, the motor speed (normalized) is plotted against time. As shown, after an acceleration phase, the motor speed reaches a desired constant speed after which time the probe begins to puncture the container seal 20. During this period of seal penetration, the motor speed wavers slightly until the probe tip encounters the container bottom. Thereafter, the motor speed drops precipitously. When the motor velocity drops below a predetermined threshold, say, 75% of its normalized constant speed, the microprocessor operates to immediately de-energize motor 16, thereby maintaining the probe tip in contact with the container bottom and ready for sample aspiration.

It will be appreciated that the lead screw used to advance the aspiration probe is just one mechanism for translating the motor rotation into a linear (vertical) movement of the probe. A gear-rack and pinion scheme could also be used to provide this translation. In such case, a motor having a drive shaft, as opposed to a rotatably-driven nut 22, supports a pinion for rotation, the latter serving to drivingly engage a linear rack of gear teeth to which the aspiration probe is coupled. The encoder disk 24 will rotate with the motor shaft, and its radially-extending indicia will be sensed as described above to arrest movement of the probe when it reaches the container bottom. Further, it will be appreciated that the principle of the invention applies to both D.C. and stepper motors; but for stepper motors the sensing of motor stalling is easier. In driving the stepper motor, a series of electrical pulses (steps) at a certain rate are applied to the stepper motor by the microprocessor. The total stepper motor movement is directly related to the number of pulses, while the stepper motor speed is proportional to the rate (frequency) of the pulses. Preferably, the encoder associated with the stepper motor produces ticks (pulses) at a rate having a direct relationship with the driving pulses. As the encoder ticks lag behind the driving pulses, it indicates that the stepper motor is beginning to stall. Another variation is to use a linear actuator for the probe-advancing drive motor, and to employ the output of a linear encoder to sense a stalling of the motor (and a sudden drop in the movement of the actuator) as occurs when the probe tip encounters the container bottom.

While the invention has been described in detail with reference to preferred embodiments, it will be apparent that modifications and variations can be made without departing from the spirit of the invention, and reference should be made to the appended claims to ascertain the true scope of the invention.

What is claimed is:

1. Apparatus for aspirating a volume of liquid from a liquid-containing vessel, said apparatus comprising:
   (a) a liquid-aspirating probe having a tip through which liquid in a vessel can be aspirated;
   (b) a motor comprising a movably-mounted driven member operatively connected to said aspiration probe and adapted to advance said probe tip into a vessel containing liquid to be aspirated as said driven member is moved by said motor in a first direction;
   (c) means operatively coupled to the driven member for producing a signal indicating the instantaneous speed of movement and/or position of said driven member, said signal-producing means comprising an encoder adapted to produce a series of pulses, each reflecting an incremental movement of said driven member; and
   (d) a motor controller, responsive to said signal, for arresting the movement of said driven member in the event said signal indicates that advancement of said probe tip has been resisted by contact with a wall of the vessel, said motor controller operating to arrest movement of said driven member in the event one or more of said pulses are not produced within a predetermined time interval and/or in the event there is an abrupt reduction in the rate at which said pulses are produced by said encoder.

2. The apparatus as defined by claim 1 wherein said motor comprises a stepper motor.

3. The apparatus as defined by claim 1 wherein said motor comprises a D.C. motor.

4. The apparatus as defined by claim 1 wherein said motor comprises a linear actuator.

5. Apparatus for aspirating a volume of liquid from a liquid-containing vessel, said apparatus comprising:
   (a) a liquid-aspirating probe having a tip through which liquid in a vessel can be aspirated;
   (b) a motor comprising a movably-mounted driven member operatively connected to said aspiration probe and adapted to advance said probe tip into a vessel containing liquid to be aspirated as said driven member is moved by said motor in a first direction;
   (c) means operatively coupled to the driven member for producing a signal indicating the instantaneous speed of movement and/or position of said driven member, said signal-producing means comprising an encoder adapted to produce a series of pulses, each reflecting an incremental movement of said driven member; and
   (d) a motor controller, responsive to a predetermined change in a pattern of pulses produced by the encoder indicating that movement of the probe tip has been resisted by the vessel bottom, for arresting the movement of said driven member.

* * * * *